United States Patent [19]

Fan

[11] Patent Number: 5,100,402
[45] Date of Patent: Mar. 31, 1992

[54] ELECTROSURGICAL LAPAROSCOPIC CAUTERIZATION ELECTRODE

[75] Inventor: Peter Fan, Hakensack, N.J.

[73] Assignee: MegaDyne Medical Products, Inc., Murray, Utah

[21] Appl. No.: 593,194

[22] Filed: Oct. 5, 1990

[51] Int. Cl.$^5$ .................................................. A61B 17/39
[52] U.S. Cl. ........................................ 606/41; 606/45; 606/49
[58] Field of Search ........................ 606/37, 39, 40, 41, 606/45–50, 170; 128/751, 754

[56] References Cited

U.S. PATENT DOCUMENTS

| | | | |
|---|---|---|---|
| 4,411,657 | 10/1983 | Galindo | 604/274 |
| 4,785,807 | 11/1988 | Blanch | 606/45 |
| 4,919,129 | 4/1990 | Weber, Jr. et al. | 606/42 |

Primary Examiner—Stephen C. Pellegrino
Assistant Examiner—Steven J. Shumaker
Attorney, Agent, or Firm—Sigalos & Levine

[57] ABSTRACT

A laparoscopic cauterization electrode for connection to a source of appropriate electrical power for performing deep surgical operations through an opening in a body such as deep thorax, abdominal perineal, deep rectum, deep gynecological and similar deep body operations, comprising an electrically conductive electrode shaft of a width sized for insertion through the body opening having a proximal and a distal end, the proximal the of said electrode adapted for electrical connectivity to the power source and the distal end having teflon-coated operative tip associated therewith, insulation for providing both electrical and thermal insulation and abrasion resistance along the electrode shaft between the proximal and distal ends of the electrode and the electrode shaft being of a sufficient length to extend from the exterior into the interior of a body for performing the deep surgical operations.

4 Claims, 1 Drawing Sheet

ELECTROSURGICAL LAPAROSCOPIC CAUTERIZATION ELECTRODE

BACKGROUND AND FIELD OF THE INVENTION

The present invention relates to a surgical electrode for use in laparoscopic surgery and in particular to an instrument designed for deep surgical procedures involving tissue separation, dissection, and cauterization; as for example, deep thorax, intra-abdominal, deep rectum, and deep gynecological operations.

Laparoscopy has long been a standard form of treatment for gynecologic diseases and more recently has shown some promise in general surgical disorders, for example, certain abdominal disorders such as cholelithiasis, appendicitis, and intra-abdominal adhesions. The use of laparoscopy in general surgery has increased in recent years with the increased usage of laser energy for cutting and coagulation. Other modes of cutting energy include scissors, endothermic and electrical energy.

In general laparoscopy is performed by inserting a scope through one trocar or sheath and a surgical instrument through one or more other trocars or sheaths. The trocars are sleeves which are inserted through a body opening which may be a surgically made opening or portal through the skin, muscle and peritoneal membrane. The trocar typically has an inside diameter of 10 millimeters. The instrument for insertion through the trocar typically has an outside diameter of about 5 millimeters. Often the body cavity, such as the abdominal peritoneal area is inflated with low pressure carbon dioxide. An insufflation pressure of about 12 millimeters of HG or less is maintained during the operation by a sealing membrane located in the trocar opening comprising a thin rubber material having a small diameter hole of approximately 3 millimeters therein. The 5 millimeter diameter instrument is inserted through the membrane hole which stretches to accommodate the larger size thereby forming and effective seal.

Each of the forms of cutting energy used in laparoscopy have certain limitations and drawbacks. In particular, laser cutting and coagulation is a slow tedious, time consuming and costly procedure. The instrumentation required is highly sophisticated and expensive. Each pass of the laser beam at safe energy levels results in a shallow cut. Any smoke resulting from the cut and cauterization can interfere with subsequent laser beam passes. The smoke diffuses the energy from the cut area requiring additional time and/or procedures for clearing the body cavity of smoke.

Scissors, of course, are useful and can be manipulated within the body cavity, however, the dissection with the use of scissors does not simultaneously cauterize and requires additional steps to stop the bleeding and to keep the operating area clear of blood. Where electrical cauterizing energy is used at the scissor blades, tissue sticks to the blades and pulls loose causing bleeding and requiring a repeated removal of the scissors for cleaning.

Endothermic has limited applications and requires complex procedures for its proper usage.

The use of electrical energy with prior known blade configurations including hook electrodes and spade electrodes are subject to various common drawbacks as well as specific drawbacks with respect to each type of electrode. Both electrodes can accomplish cutting and cauterizing to a certain degree simultaneously. However, the electrode cutting results in substantial charring of the tissue cut. There is a significant amount of smoke generated within the body cavity, thereby obstructing the view of the surgeon through the laparoscope. Further, on prior known laparoscopic instruments the charred tissue sticks to either the hook or the spatula electrode surface which often causes tearing and pulling of the tissue, thereby re-opening the previous cauterized cut area to bleeding. The build up of tissue on the electrode surface interferes with transfer of electrical energy so that the electrode must be withdrawn periodically and repeatedly for cleaning before continuing the operation.

Specifically, hook electrodes, as the name implies, are used to go around a structure or tissue such as a duct or an artery, thereby pulling the structure away from surrounding tissue while the electrical energy is applied. This often results in cumbersome procedures for engaging and then disengaging the electrode to complete the surgical procedure. A Hook electrode may be used to pull tissue sideways to the right or to the left, but in changing from one to the other, the hook electrode must be turned 180° along its long axis, making it inconvenient to use.

Spatula electrodes are pointed instruments having one concave surface and an opposed convex surface, and typically have a hole through the face of the spade-shaped tip to allow smoke to escape. Spatula electrodes are not well adapted for pushing or pulling tissues for the separation thereof because of the curved edges of the blade which terminates at a point and also because of the surface convexity and concavity, and they cannot pull tissue edgeways, or hold tissue with a edgeways pull.

BRIEF DESCRIPTION OF THE DRAWINGS

Applicant's invention overcomes many of the above identified problems associated with previously used laparoscopic surgical instruments. Other objects and other advantages will be understood with reference to the following drawings in which like numerals represent like elements and in which.

SUMMARY OF THE INVENTION

Figure 1:
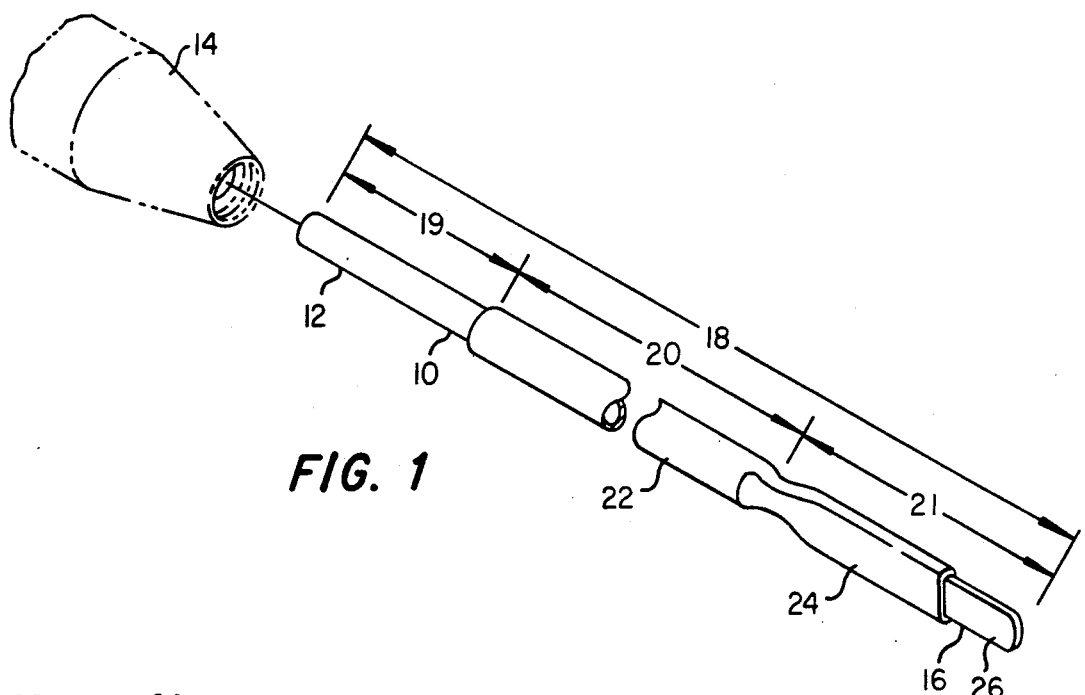
FIG. 1 is a schematic perspective view of the electrode according to the preferred embodiment with a hand-held pencil RF electrical source shown in phantom lines.

The invention comprises a cauterizing and dissecting electrode with a specially designed operative means such as a tip or blade. The electrode is specially elongated and is insulated along its length for use in deep laparoscopic procedures. The effective use is facilitated with a hand-operated switch for applying electrical energy from a power source. The various features of the electrode in one or more unique combinations provide unique and unobvious advantages for laparoscopic surgery. Preferably the tip is a specially shaped blade with parallel flat sides, thin parallel edges with the nose being blunt, and almost square with rounded corners. This special shape allows the laparoscopic instrument to be used for multiple functions during surgery rather than just for a single function as with previously known electrodes. For example, the broad surface of the flat blade can be used for electro-cautery of large bleeder areas. The thin edge of the blade can be used simultaneously for cutting and cauterizing, the blunt and almost square nose can be used effectively for blunt dissection, allowing the proper plane of separation to be easily followed; as for example, when a Gall-bladder is removed from its bed within the liver. The entire length of the long electrode shaft is provided with an insulative coating between the proximal end and the distal end of the electrode. The insulative coating advantageously extends downward partially along the length of the thin flat blade surface leaving only a short portion of the blade exposed for application of RF electrical energy during surgery. The long electrically insulated shaft allows sufficient leverage for manual manipulation of tissues into proper position and for blunt dissection. The straight flat edge of the blade can be used to hold fibrous strands or the peritoneal coat in position while cautery is applied at the exposed tip, especially in an edgeways manner. The unique and advantageous configuration is further facilitated in one preferred embodiment where the tip is uniquely coated with a non-stick coating such as teflon, having a substantially uniform thickness which permits the application of RF electrical energy for cauterization. The entire electrode including length, insulated shaft and teflon coated blade is designed to minimize tissue charring and tissue sticking to the electrode, continuous and repeated withdrawal for cleaning is not required as with exposed metal cauterization electrodes.

Adapting the electro-surgical laparoscopic instrument for use with a hand switch as opposed to previously known foot switches advantageously permits the use of only hand-eye coordination and does not require hand-eye-foot coordination which is typically less precise. Often when using a foot switch, much time is wasted in fumbling around with the foot and having to take the eyes away from the video screen to look for the foot switch.

The use of electro-cautery blades in the deep body cavity laparoscopic procedures avoids the high cost of a laser machine including the high cost of maintenance, the high cost of disposable single-use yag laser fibers and saves much wasted nuisance and time. Surgeons are required to be "privileged" in laser use in their own hospital which requires the extra expense of special laser nurses, the need to take special precautions, posting of signs, wearing of special mask, wearing of special goggles and the use of special smoke evacuators as small amounts of cauterization smoke will interfere with the laser beam. Hook up of the machine, warm up and testing also require additional time and technicians in the operating room. Further, firing of the laser almost invariably results in the blurring of the laparoscopic video screen because of the high energy discharge, molecular ionization, and high frequency electromagnetic wave forms resulting from the laser. Further, the complexity of a laser machine reduces its reliability and break downs can result in the middle of a surgical procedure. The time to repair of "down-time" is usually significant. Further, the target for laser cauterization has to be clearly and directly exposed as laser light will not go sideways, around corners, or up and under and around soft tissues. The inventive long leverage solid insulated probe can easily push past soft tissues, hold them in place and cut and cauterize only the intended area.

DETAILED DESCRIPTION OF THE DRAWINGS

The various other advantages of the inventive laparoscopic cauterization electrode will be described in connection with the drawings and in particular, in connection with Gall-bladder removal or Cholecystectomy.

FIG. 1 shows a schematic prospective view of an electro surgical laparoscopic cauterization electrode 10. The electrode has a proximal end 12 adapted for electrical connection with a hand-held RF electrical source pencil 14. Advantageously a hand-held pencil is used with a hand or finger operated switch (not shown) for returning the transfer of RF electrical energy to the electrode. A blade 16 is formed on the distal end of the electrode so that an over all length 18 is provided which is sufficiently long to extend from the exterior to the interior of a body cavity for performing a deep laparoscopic surgery. The over all length 18 includes the electrical connection end 12 length 19 plus the electrode body 10 length 20 plus the blade 16 length 21. The electrode shaft body 10 can be formed of stainless steel and is preferably a solid rod or a sufficiently thick-walled tube to provide adequate strength for the leverage provided by the uniquely long length, preferably the length will be in the range of about 18 cm (7 inches) to about 41 cm (about 16 inches).

The shaft body along length 19 is typically exposed so that direct electrical connection can be made between connector end 12 and RF source 14. An insulating coating 22 may advantageously be formed of an electrically insulative plastic tubing which is tightly fitted onto electrode shaft 10 as for example by shrink-fitting where otherwise shrinking the insulation material tightly onto the shaft hand once it is in position. While the insulation 22 need only extend along length 20 to blade 16 in order to be useful (as will be explained further with respect to FIG. 6 below) it has been found to be advantageous to provide extended insulation material 24 partially along the length 21 of blade 16. Again, insulative coating 24 is tightly fitted and flattened onto the blade surface 26 as by thermal or heat shrink-fit as with insulative coating 22. Advantageously, insulative coating 24 is integrally formed with coating 22 and extends close to the end of Blade 16; preferably, within about 5 mm (about ¼ inch) from the end of blade 16.

Figure 2:
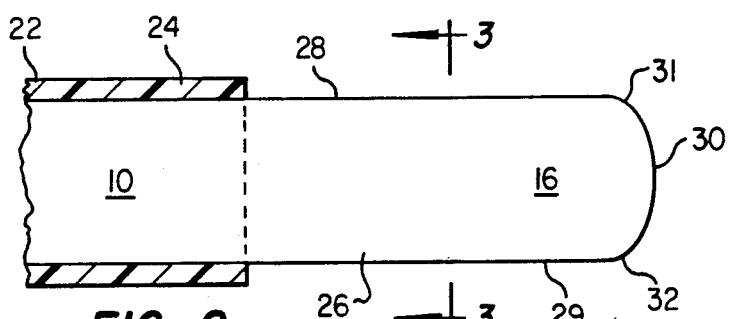
FIG. 2 is an enlarged side view of the tip of the electrode shown in partial cross-section.
Figure 3:
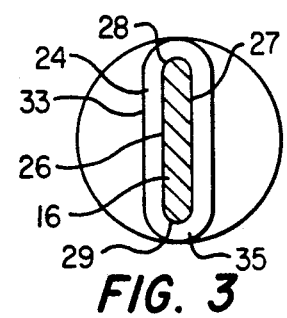
FIG. 3 is a cross-sectional view of the enlarged tip of FIG. 2 along section line 3—3.

With reference to FIGS. 2 and 3, in which FIG. 2 is a partial side view of blade 16 of electrode 10 and FIG. 3 is a cross-sectional view of blade 16 of electrode 10 taken along section line 3—3, further details of the construction of the preferred embodiment can be seen. The blade 16 has a portion which extends beyond insulative coating 22 and extended insulative coating portion 24. In the embodiment shown, the blade 16 has substantially parallel flat side portions 26 and 27 and thin blunted edge portions 28 and 29. There is a blunted almost square tip portion 30 which interconnects with edge 28 at rounded corners 31 and 32. In the embodiment as shown in FIG. 3, blade 16 is physically configured according to the present invention to advantageously perform electro-surgical operations including having the extended insulative coating 24 which allows the use of an insulated side portion 33 and an insulated edge portion 35 for pushing and holding tissues without applying electrical energy there too. Yet the nose portion 30 which is exposed metal for application of RF frequency electricity allows application of RF electrical energy to the tissues to be cut or cauterized.

Figure 4:
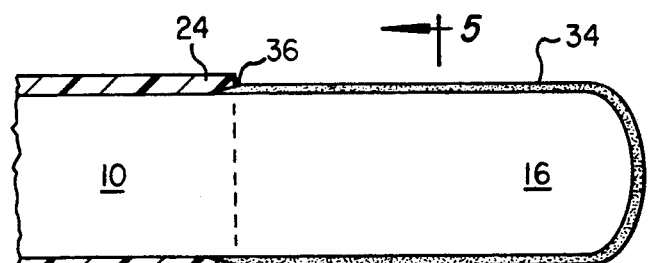
FIG. 4 is an enlarged side view shown in partial cross-section of the polytetrafluoroethylene (PTFE) coated tip according to the present invention.
Figure 5:
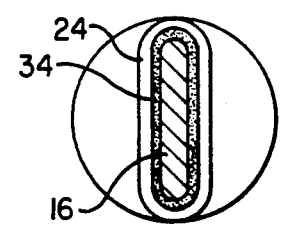
FIG. 5 is a schematic view of the electrode tip of FIG. 4 shown in partial cross-section.

With reference to FIGS. 4 and 5, the further advantageous construction including a non-stick coating 34 is depicted in partial cross-sectional view of FIG. 4 and in cross-sectional view of FIG. 5 taken along section line 5—5. It is seen that the non-stick coating 34 which may be a PTFE or fluorinated hydrocarbon material coating 24 according to U.S. Pat. Nos. 4,785,807 and 4,876,110 and completely surrounds the exposed portion of blade 16. Preferably the non-stick PTFE coating 34 tapers at 36 so that it is under insulative extension 24 as at 38 thereby avoiding any exposed bare metal electrode 10 which may inadvertently stick to tissues during laparoscopic surgical procedures.

Figure 6:
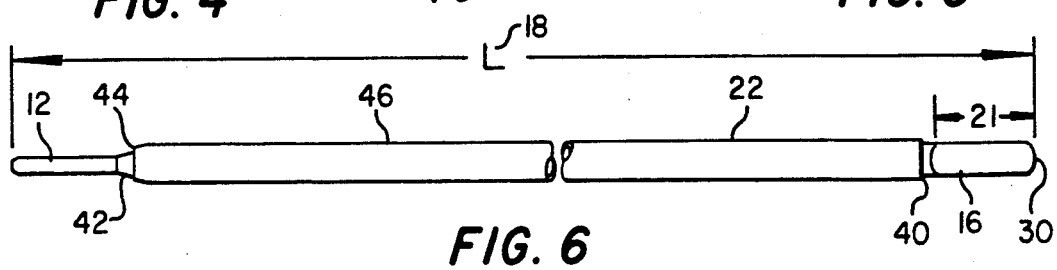
FIG. 6 is a side view of an alternative embodiment of an electrode according to the present invention.

With reference to FIG. 6, which is a side plan view of a long electro-surgical laparoscopic electrode according to an alternative embodiment of the present invention it can be seen again that the length 18 is sufficiently long for deep surgical operations. Preferably the length will be greater than about 18 cm (7 inches) and shorter than about 41 cm (16 inches). This length range allows for sufficient extension into the body cavity for most of the deepest body cavity operations yet allows the operator sufficiently precise blade tip control from a hand held RF electrically energy source pencil. In the embodiment shown, the insulative plastic coating 22 terminates at a distal end 40 substantially adjacent to the blade 16 at a length 21 from the distal tip 30. In this embodiment the electrical connector portion 12 has a smaller diameter than the length 20 and has a taper portion 42 expanding the diameter sufficient such that in combination with the thickness of coating 22 a standard diameter shaft 46 results. Preferably the entire diameter 46 and surface of plastic coating 22 is the same diameter along the entire length 20 and is sufficiently smooth to provide an air tight inter-connection through the sealing membrane of a standard trocar with which it may be used (trocar and sealing membrane not shown).

While the invention has been described in connection with preferred embodiments, it is not intended to limit the scope of the invention to the particular embodiment set forth, but, on the contrary, it is intended to cover such alternatives, modifications, and equivalents as may be included within the spirit and scope of the invention as defined by the appended claims.

What is claimed is:

1. A laparoscopic cauterization electrode for connection to a source of appropriate electrical power for performing deep surgical operations through an opening in a body such as deep thorax, abdominal perineal, deep rectum, deep gynecological and similar deep body operations, comprising:
   (a) an electrically conductive electrode shaft of a width sized for insertion through said body opening, having a proximal and a distal end;
   (b) insulating means for providing both electrical and thermal insulation and abrasion resistance along said electrode shaft between said proximal and distal ends of said electrode;
   (c) said proximal end of said electrode adapted for electrical connectivity to said power source and said distal end having polytetrafluoroethylene-coated operative means associated therewith; said polytetrafluoroethylene-coated operative means comprising: (1) a flat blade rigidly connected to said electrode shaft having substantially parallel flat sides, substantially parallel thin straight edges, and a blunt nose inter-connection with said straight edges at rounded corners; and (2) a smooth thin continuous layer of polytetrafluoroethylene covering said sides, edges, nose and corners;
   (d) said electrode shaft being of a sufficient length to extend from the exterior into the interior of a body for performing said deep surgical operations; and
   (e) wherein said insulating means is a smooth continuous coating of electrical and thermal insulation material extending along said electrode shaft terminating adjacent to said proximal end so that a bare shaft is exposed at said proximal end for electrical connection and said insulation terminating adjacent said polytetrafluoroethylene-coated blade at said distal end so that said operative means is exposed for application of electrical energy during said deep surgical operation.

2. A laparoscopic cauterization electrode according to claim 1 in which said electrode shaft is of a sufficient length within a range of about 18 cm to about 41 cm to extend from the exterior into the interior of a body for performing deep surgical operations.

3. A laparoscopic cauterization electrode for connection to a source of appropriate electrical power for performing deep surgical operations through an opening in a body such as deep thorax, abdominal perineal, deep rectum, deep gynecological and similar deep body operations, comprising:
   (a) an electrically conductive electrode shaft of a width sized for insertion through said body opening, having a proximal and a distal end;
   (b) insulating means for providing both electrical and thermal insulation and abrasion resistance along said electrode shaft between said proximal and distal ends of said electrode;
   (c) said proximal end of said electrode adapted for electrical connectivity to said power source and said distal end having polytetrafluoroethylene-coated operative means associated therewith; said polytetrafluoroethylene-coated operative means comprising: (1) a flat blade rigidly connected to said electrode shaft having substantially parallel flat sides, substantially parallel thin straight edges, and a blunt nose inter-connection with said straight edges at rounded corners; and (2) a smooth thin continuous layer of polytetrafluoroethylene covering said sides, edges, nose and corners;
   (d) said electrode shaft being of sufficient length to extend from the exterior into the interior of a body for performing said deep surgical operations; and
   (e) wherein said insulating means is a smooth continuous coating of electrical and thermal insulation material extending along said electrode shaft terminating adjacent said proximal end so that electrical connection can be made therewith and having an extension of said insulating material partially onto said polytetrafluoroethylene-coated blade such that only a short portion of said blade sides, edges, nose and corners are exposed for application of electrical energy during said deep surgical operation.

4. A laparoscopic cauterization electrode according to claim 3 in which said electrode shaft is of a sufficient length within a range of about 18 cm to about 41 cm to extend from the exterior into the interior of a body for performing deep surgical operations.

* * * * *